United States Patent
Goetz et al.

(10) Patent No.: US 7,848,819 B2
(45) Date of Patent: Dec. 7, 2010

(54) MEDICAL DEVICE PROGRAMMING SAFETY

(75) Inventors: Steven M. Goetz, Brooklyn Center, MN (US); Donald R. Johnson, Lino Lakes, MN (US); Touby A. Drew, Golden Valley, MN (US); Andrew H. Houchins, Lino Lakes, MN (US); Jeffrey T. Keacher, Stanford, CA (US); Theodore J. Stone, St. Louis Park, MN (US); Earle T. Roberts, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 408 days.

(21) Appl. No.: 11/940,573

(22) Filed: Nov. 15, 2007

(65) Prior Publication Data

US 2008/0140161 A1 Jun. 12, 2008

Related U.S. Application Data

(60) Provisional application No. 60/873,190, filed on Dec. 6, 2006, provisional application No. 60/873,264, filed on Dec. 6, 2006.

(51) Int. Cl.
*A61N 1/08* (2006.01)

(52) U.S. Cl. .............................. 607/59; 607/31; 607/63

(58) Field of Classification Search ........................ None
See application file for complete search history.

(56) References Cited

U.S. PATENT DOCUMENTS

| | | | |
|---|---|---|---|
| 3,942,535 A | | 3/1976 | Schulman |
| 4,208,008 A | * | 6/1980 | Smith .......................... 714/811 |

(Continued)

FOREIGN PATENT DOCUMENTS

EP    0 750 921 A2    1/1997

(Continued)

OTHER PUBLICATIONS

Khalessi, A. A., Taylor, R. S., Brigham, D. D., North, R. B., "Automated, patient-interactive spinal cord stimulator adjustment: A cost-minimization analysis," Neurosurgery, 53:501-502, Aug. 2003.

(Continued)

*Primary Examiner*—Kennedy J Schaetzle
(74) *Attorney, Agent, or Firm*—John W. Albrecht; Shumaker & Sieffert

(57) ABSTRACT

Techniques for increasing the safety of medical device programming using general purpose hardware, such as a general purpose personal computer, are described. Some embodiments include a watchdog module that is serviced by the general purpose hardware, a mediator module that monitors programming instructions from the general purpose hardware, and/or a safe mode input that may be activated by a user. In some embodiments, a system comprises an implantable medical device, an intermediate device, a computing device that communicates with the implantable medical device via the intermediate device. The intermediate device may provide any one or more of the safety measures described above. In some embodiments, the intermediate device is dedicated hardware, and critical programming functions are provided by the intermediate device, rather than the general purpose hardware. In some embodiments, an implantable medical device provides one or more of the above-discussed safety features, rather than a separate intermediate device.

19 Claims, 5 Drawing Sheets

U.S. PATENT DOCUMENTS

| | | | |
|---|---|---|---|
| 4,304,238 A * | 12/1981 | Fischer | 607/31 |
| 4,365,633 A * | 12/1982 | Loughman et al. | 607/30 |
| 4,550,732 A | 11/1985 | Batty, Jr. et al. | |
| 4,587,970 A * | 5/1986 | Holley et al. | 607/15 |
| 4,926,865 A | 5/1990 | Oman | |
| 5,158,078 A * | 10/1992 | Bennett et al. | 607/27 |
| 5,226,413 A * | 7/1993 | Bennett et al. | 607/18 |
| 5,350,407 A | 9/1994 | McClure et al. | |
| 5,383,915 A | 1/1995 | Adams | |
| 5,456,692 A | 10/1995 | Smith, Jr. et al. | |
| 5,653,735 A | 8/1997 | Chen et al. | |
| 5,683,432 A * | 11/1997 | Goedeke et al. | 607/32 |
| 5,690,690 A | 11/1997 | Nappholz et al. | |
| 5,752,977 A | 5/1998 | Grevious et al. | |
| 5,792,201 A * | 8/1998 | Causey et al. | 607/27 |
| 5,938,690 A | 8/1999 | Law et al. | |
| 6,249,703 B1 | 6/2001 | Stanton et al. | |
| 6,308,102 B1 * | 10/2001 | Sieracki et al. | 607/59 |
| 6,480,745 B2 | 11/2002 | Nelson et al. | |
| 6,516,227 B1 | 2/2003 | Meadows et al. | |
| 6,577,899 B2 | 6/2003 | Lebel et al. | |
| 6,597,951 B2 * | 7/2003 | Kramer et al. | 607/9 |
| 6,609,032 B1 * | 8/2003 | Woods et al. | 607/46 |
| 6,622,045 B2 * | 9/2003 | Snell et al. | 607/30 |
| 6,659,968 B1 | 12/2003 | McClure | |
| 6,665,565 B1 | 12/2003 | Stomberg et al. | |
| 6,804,558 B2 | 10/2004 | Haller et al. | |
| 6,868,309 B1 | 3/2005 | Begelman | |
| 6,878,112 B2 | 4/2005 | Linberg et al. | |
| 6,895,280 B2 | 5/2005 | Meadows et al. | |
| 6,978,181 B1 * | 12/2005 | Snell | 607/60 |
| 7,043,305 B2 | 5/2006 | KenKnight et al. | |
| 7,060,031 B2 * | 6/2006 | Webb et al. | 600/300 |
| 7,065,409 B2 | 6/2006 | Mazar | |
| 7,142,923 B2 | 11/2006 | North et al. | |
| 7,146,219 B2 | 12/2006 | North et al. | |
| 7,155,290 B2 * | 12/2006 | Von Arx et al. | 607/60 |
| 7,181,286 B2 | 2/2007 | North et al. | |
| 7,216,000 B2 | 5/2007 | North et al. | |
| 7,489,970 B2 * | 2/2009 | Lee et al. | 607/46 |
| 7,610,099 B2 * | 10/2009 | Almendinger et al. | 607/60 |
| 7,657,319 B2 * | 2/2010 | Goetz et al. | 607/59 |
| 2002/0016568 A1 | 2/2002 | Lebel et al. | |
| 2002/0049480 A1 | 4/2002 | Lebel et al. | |
| 2002/0123673 A1 * | 9/2002 | Webb et al. | 600/300 |
| 2002/0133207 A1 | 9/2002 | Thomas et al. | |
| 2003/0088290 A1 | 5/2003 | Spinelli et al. | |
| 2003/0130708 A1 | 7/2003 | Von Arx et al. | |
| 2003/0177031 A1 | 9/2003 | Malek | |
| 2004/0138518 A1 | 7/2004 | Rise et al. | |
| 2004/0138724 A1 * | 7/2004 | Sieracki et al. | 607/60 |
| 2004/0143302 A1 | 7/2004 | Sieracki et al. | |
| 2004/0167587 A1 | 8/2004 | Thompson | |
| 2004/0199215 A1 * | 10/2004 | Lee et al. | 607/48 |
| 2004/0215286 A1 | 10/2004 | Stypulkowski | |
| 2004/0260363 A1 * | 12/2004 | Arx et al. | 607/60 |
| 2005/0277999 A1 * | 12/2005 | Strother et al. | 607/48 |
| 2005/0283198 A1 | 12/2005 | Haubrich et al. | |
| 2006/0161213 A1 | 7/2006 | Patel | |
| 2006/0190047 A1 * | 8/2006 | Gerber et al. | 607/41 |
| 2008/0140161 A1 * | 6/2008 | Goetz et al. | 607/60 |
| 2008/0140162 A1 * | 6/2008 | Goetz et al. | 607/60 |
| 2009/0157137 A1 * | 6/2009 | Gilkerson et al. | 607/31 |

FOREIGN PATENT DOCUMENTS

| | | |
|---|---|---|
| EP | 0 753 327 A2 | 1/1997 |
| WO | WO02/057994 A2 | 7/2002 |
| WO | WO 03/092769 A2 | 11/2003 |

OTHER PUBLICATIONS

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, Mar. 2003.

Fowler, K.R., "Neurological Stimulation System", Proceedings AAMI 21st Annual Meeting, Apr. 12-16, p. 27, 1986.

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation For Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

U.S. Appl. No. 10/696,491, entitled "Body Region Indication", filed Oct. 29, 2003, Richard B. North, Jeffrey M. Sieracki.

U.S. Appl. No. 10/696,725, entitled "Failsafe Programming of Implantable Medical Devices", filed Oct. 29, 2003, Richard B. North, Jeffrey M. Sieracki.

Sieracki et al., U.S. Appl. No. 12/038,364 entitled "Failsafe Programming of Implantable Medical Devices", filed Feb. 27, 2008.

Keacher et al., U.S. Appl. No. 11/940,604 entitled "Medical Device Programming Safety," filed Nov. 15, 2007.

Keacher et al., U.S. Appl. No. 11/940,734 entitled "Telemetry Device for a Medical Device Programmer," filed Nov. 15, 2007.

Request for Continued Examination Transmittal and Response to Final Office Action for U.S. Appl. No. 10/696,725, dated Oct. 15, 2007 (14 pgs.).

Advisory Action for U.S. Appl. No. 10/696,725, dated Sep. 27, 2007 (6 pgs.).

Response to Final Office Action for U.S. Appl. No. 10/696,725, dated Sep. 13, 2007 (15 pgs.).

Final Office Action for U.S. Appl. No. 10/696,725, dated Jul. 13, 2007 (8 pgs.).

Response to Office Action for U.S. Appl. No. 10/696,725, dated Apr. 4, 2007 (20 pgs.).

Office Action for U.S. Appl. No. 10/696,725, dated Dec. 5, 2006 (8 pgs.).

Response to Restriction Requirement for U.S. Appl. No. 10/696,725, dated Aug. 18, 2006 (12 pgs.).

Restriction Requirement for U.S. Appl. No. 10/696,725, dated Jul. 18, 2006 (6 pgs.).

Notification of Transmittal of the International Preliminary Report on Patentability for corresponding patent application No. PCT/US2007/024096, mailed Mar. 17, 2009, 9 pages.

Notification of Transmittal of the International Search Report and the Written Opinion for corresponding patent application No. PCT/US2007/024096, mailed Jun. 6, 2008, 24 pages.

Reply to Written Opinion for corresponding patent application No. PCT/US2007/024096, filed Sep. 5, 2008, 14 pages.

Reply to Written Opinion for patent application No. PCT/US2007/023817, filed Sep. 30, 2008, 12 pages.

Office Action from U.S. Appl. No. 11/940,604, dated Apr. 5, 2010, 20 pp.

Response to Office Action dated Apr. 5, 2010, from U.S. Appl. No. 11/940,604, filed Jul. 6, 2010, 17 pp.

Office Action dated Jun. 3, 2010 for U.S. Appl. No. 12/038,364 (12 pgs.).

Responsive Amendment dated Aug. 31, 2010 for U.S. Appl. No. 12/038,364 (14 pgs.).

* cited by examiner

US 7,848,819 B2

MEDICAL DEVICE PROGRAMMING SAFETY

This application claims the benefit of U.S. Provisional Application No. 60/873,190 to Goetz et al., entitled "MEDICAL DEVICE PROGRAMMING SAFETY," and filed on Dec. 6, 2006 and U.S. Provisional Application No. 60/873,264 to Keacher et al., entitled "TELEMETRY MODULE FOR A MEDICAL DEVICE PROGRAMMER," filed on Dec. 6, 2006. The entire content of each of these provisional applications is incorporated herein by reference.

TECHNICAL FIELD

The invention relates to medical devices and, more particularly, to medical device programming.

BACKGROUND

Clinicians and patients typically communicate with an implantable medial device (IMD) using a clinician programmer (CP) and patient programmer, i.e., patient therapy manager (PTM), respectively. A clinician may use a CP to perform advanced IMD setup and diagnostics, while the PTM typically provides a less feature-rich interface for the patient to interact with the IMD. For example, while both the CP and PTM may be used to "program" an IMD and receive diagnostic information from the IMD, the PTM may generally only able to make limited programming modifications, and receive limited diagnostic information that is relevant to the patient, e.g., battery status. Both the CP and the PTM have traditionally communicated directly with the IMD for programming the IMD.

CPs and PTMs are computing devices. Traditionally, these computing devices have been special-purpose devices, i.e., dedicated to tasks associated with programming or otherwise communicating with IMDs. For example, these computing devices generally run custom operating systems, and only have software supporting CP or PTM functionality loaded thereon. Further, these computing devices are typically limited in their input/output capabilities, e.g., to communication with IMDs and, in some cases, each other.

SUMMARY

In general, the invention is directed to techniques that facilitate use of an off-the-shelf, general purpose computer as a CP. For example, CP software could be run on computers that already exist in a clinic for other functions, such as interfacing with a clinic network to access electronic medical records, scheduling, or billing systems. The general purpose computer may be a desktop, laptop, or tablet computer running a commercial operating system, such as Windows XP or Windows Vista, made commercially available by Microsoft Corporation of Redmond, Wash. Using an off-the-shelf, general purpose computer as a CP may reduce the amount of computer hardware needed in the clinic, which, from the perspective of the clinic, may save space and money.

However, there are safety and regulatory concerns associated with using an off-the-shelf, general purpose computer as a CP. Dedicated, special purpose CPs are relatively safe and secure, because of their custom operating system, limited communication capabilities, and the lack of conflicting software applications. On the other hand, off-the-shelf computing devices in clinics are typically networked and run common desktop operating systems, and thus are prone to computer viruses or other security threats. Risks associated with use of a general purpose, off-the-shelf computing device as a CP include possible conflicts for resources with other programs within the desktop, effects of viruses or other corruption of the desktop applications, or other disruptions of the expected operation of the desktop.

These risks are a concern with respect to use of the computer for other clinic functions. These risks become an exponentially more serious concern when communicating with an IMD. For example, disruptions caused by a virus or other corruption could result in transmission of repeated, spurious or erroneous commands to the IMD. Such commands may result in unintended, and possibly harmful, changes to the therapy delivered to the patient. Additionally, such disruptions may interrupt the flow of information from the IMD to the computing device used for programming. For example, if the therapy delivered by the IMD is altered or suspended awaiting an action from the IMD (e.g., performing a measurement and transferring the measurement data to the computing device), disruption of the flow of information may prevent the planned restoration of proper therapy.

Techniques according to the invention may facilitate safer use of an off-the-shelf, general purpose computer as a CP. Some embodiments include a watchdog module that is serviced by the general purpose CP, a mediator module that monitors programming instructions from the general purpose CP, and/or a safe mode that may be manually activated by a user or automatically activated based on signals detected via the watchdog and/or the system mediator. In some embodiments, a system comprises a dedicated, special purpose intermediate device in the communication path between the general purpose computer and the IMD. This intermediate device may employ any of these techniques to provide a layer of security and safety between the off-the-shelf components and the implanted device. In some embodiments, the intermediate device may be a dedicated, special purpose PTM.

For example, in some embodiments, the intermediate device may include a watchdog module that is serviced by the CP. Failure of the CP to service the watchdog module may indicate a disruption in some aspect of the CP operation or another situation that compromises the integrity of signals from the CP to the IMD. In response to the failure of the CP to service the watchdog, the intermediate device may take an action, such as placing the IMD in a known safe mode, which may include stopping delivery of therapy or reverting to last known therapy parameters that yielded acceptable results. The safe mode may be device, clinician, therapy and/or patient specific. The safe mode may be configurable during device or application setup and may depend upon the patient needs and/or the type of therapy delivered by the IMD.

As another example, the intermediate device may analyze programming instructions received from the CP prior to communicating the instructions to the IMD. Based on the analysis, the intermediate device may determine whether the instructions are logically valid. If the instructions are not logically valid, the intermediate device may not provide the instructions to the IMD, and may also place the IMD in a known safe mode.

Further, the intermediate device may in some embodiments include a safe mode button or another mechanism for indicating a safe mode is desired. If a user, such as the patient, determines that the therapy provided by IMD is inappropriate for any reason, including improper instructions from the CP, the user may press the safe mode button. In response to the user pressing the safe mode button, the intermediate device may place the IMD in a known safe mode. The safe mode may be customizable and may be device, clinician, therapy and/or patient specific.

Additionally or alternatively, in some embodiments, the CP software and functionality may reside in the intermediate device, and may be accessed by a user using the general purpose CP computer as a user interface. In such embodiments, the intermediate device may act as a server, and the CP as a client. The general purpose CP computer may provide access to the CP functionality on the intermediate device via a web browser. Because the CP software is run on the controlled computing environment provided by the dedicated, special purpose intermediate device, rather than the uncontrolled computing environment of the general purpose CP computer, it is less prone to the problems associated with a general purpose computer.

Moreover, although primarily described herein with respect to embodiments in which an intermediate device provides the safety functionality, the invention is not so limited. In other embodiments, an implantable medical device may additionally or alternatively include a watchdog module, mediator module, and/or a user interface for entering a safe mode. Further, in some embodiments, CP software and functionality may reside in the intermediate device, and may be accessed by a user using the general purpose CP computer as a user interface.

In one embodiment, the invention is directed towards a method comprising receiving programming instructions for a medical device from a computing device, analyzing a content of the programming instructions, determining whether the content of the programming instructions is logically valid, and transmitting the programming instructions to the medical device if the content of the programming instructions is logically valid.

In another embodiment, the invention is directed towards a system comprising a computing device and a mediator module. The mediator module receives programming instructions for a medical device from the computing device, analyzes a content of the programming instructions, determines whether the content of the programming instructions is logically valid based on the analysis, and transmits the programming instructions to the medical device if the content of the programming instructions is logically valid.

In another embodiment, the invention is directed towards a computer-readable medium comprising instructions. The instructions cause a processor to receive programming instructions for a medical device from a computing device, analyze a content of the programming instructions, determine whether the content of the programming instructions is logically valid, and transmit the programming instructions to the medical device if the content of the programming instructions is logically valid.

In another embodiment, the invention is directed towards a method comprising presenting information from an applications module of an intermediate computing device to a user via a user input terminal, where the user input terminal is separate from the intermediate computing device, and where the information includes a plurality of instructions for a implantable medical device, receiving input from the user indicating a selected instruction from the plurality of instructions, and transmitting the selected instruction to the implantable medical device.

In another embodiment, the invention is directed towards a system comprising a user input terminal comprising a display, and an intermediate computing device that is separate from the user input terminal and comprises an applications module. The intermediate computing device presents information from the applications module to a user via the display of the user input terminal, where the information includes a plurality of instructions for a implantable medical device. The intermediate coupling device is configured to receive an indication of an input from the user indicating a selected instruction from the plurality of instructions, and transmit the selected instruction to the implantable medical device.

In another embodiment, the invention is directed towards a method comprising accessing an applications module within an intermediate device via a user terminal, the applications module comprising a plurality of programming instructions for programming an implantable medical device, and providing input to indicate a selected programming instruction from the plurality of programming via a user interface of the user terminal. The intermediate device communicates the selected programming instruction to the implantable medical device.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
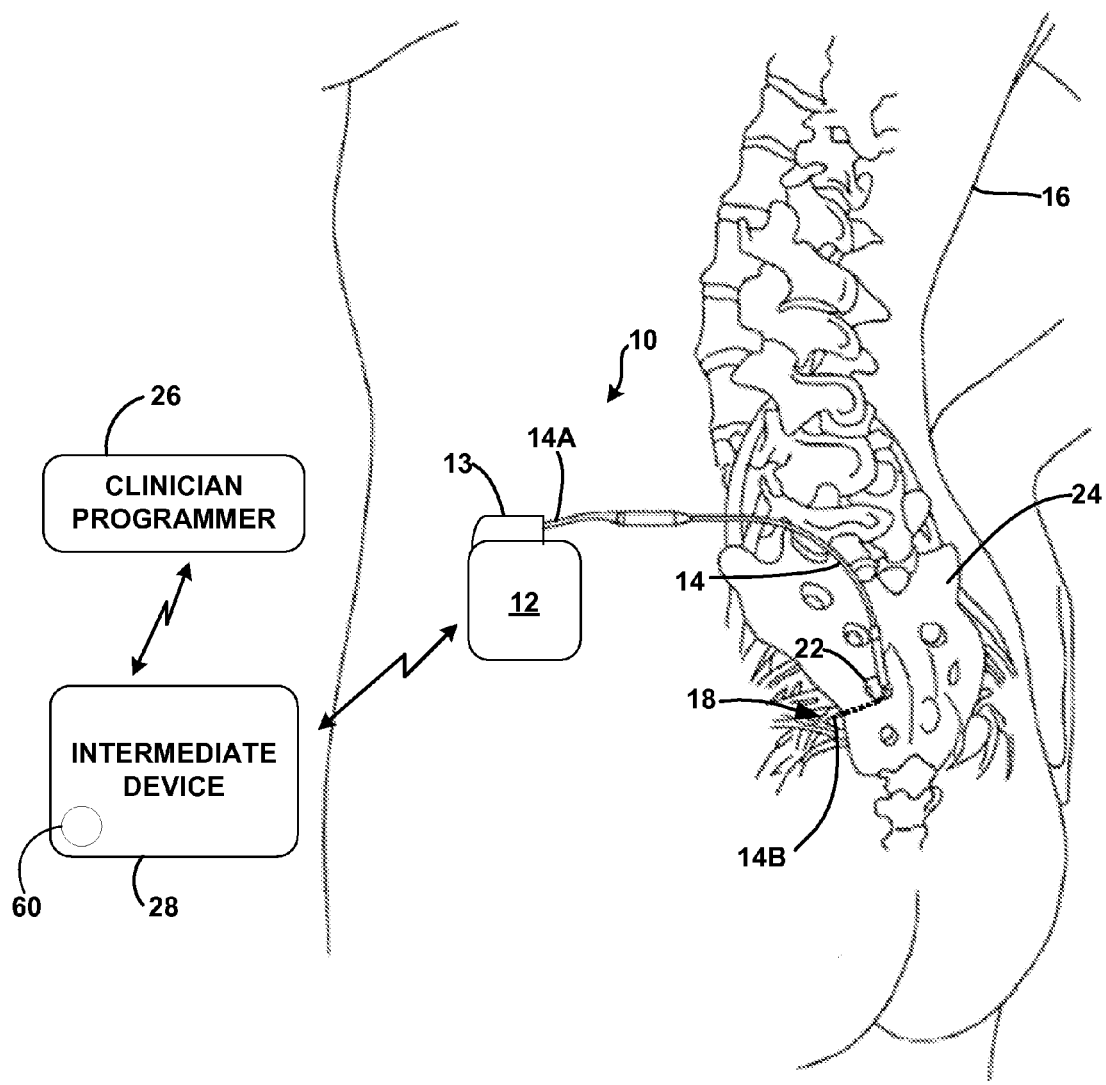
FIG. 1 is a schematic perspective view of a therapy system including an implantable medical device.

FIG. 1 is a schematic perspective view of therapy system 10, which includes implantable medical device 12 (IMD 12) with a connection port 13 and implantable medical lead 14 coupled to IMD 12. In the illustrated embodiment, IMD 12 is an electrical stimulator. However, in other embodiments, IMD 12 may be any type of implantable medical device. For example, IMD 12 may be a drug delivery device or patient monitor including one or more sensors. Accordingly, although therapy system 10 and IMD 12 are referenced throughout the remainder of the disclosure for purposes of illustration, therapy system 10 and IMD 12, in accordance with the invention, may be adapted for use in a variety of applications, such as delivery of therapeutic substances or patient monitoring via one or more sensors.

IMD 12 is coupled to stimulation lead 14 and provides a programmable stimulation signal (e.g., in the form of electrical pulses or substantially continuous-time signals) to target site 18 via stimulation lead 14. More particularly, the programmable stimulation signal is delivered to target site 18 via one or more stimulation electrodes carried by lead 14. In some embodiments, lead 14 may also carry one or more sense electrodes to permit IMD 12 to sense electrical signals from target stimulation site 18. IMD 12 may be subcutaneously implanted in the body of a patient 16 (e.g., in a chest cavity, lower back, lower abdomen, or buttocks, or on or within a cranium of patient 16), where the implant site typically depends on the target site 18 for the therapy delivery. In the example of FIG. 1, IMD 12 is an electrical stimulator that is implanted in patient 16 proximate to target stimulation site 18. IMD 12 may be referred to as a signal generator, and in the embodiment shown in FIG. 1, IMD 12 may also be referred to as a neurostimulator. In some embodiments, IMD 12 may be coupled to two or more leads, e.g., for bilateral or multilateral stimulation.

Proximal end 14A of lead 14 may be both electrically and mechanically coupled to connector 13 of IMD 12 either directly or indirectly (e.g., via a lead extension). In particular, conductors disposed in the lead body may electrically connect stimulation electrodes (and sense electrodes, if present) adjacent to distal end 14B of lead 14 to IMD 12.

In the embodiment of therapy system 10 shown in FIG. 1, target site 18 is proximate to the S3 sacral nerve, and lead 14 has been introduced into the S3 sacral foramen 22 of sacrum 24 to access the S3 sacral nerve. Stimulation of the S3 sacral nerve may help treat pelvic floor disorders, urinary control disorders, fecal control disorders, interstitial cystitis, sexual dysfunction, and pelvic pain. Therapy system 10, however, is useful in other applications. Thus, in alternate embodiments, target site 18 may be a location proximate to any of the other nerves or tissues in body 16, which may be selected based on, for example, a therapy program selected for a particular patient.

For example, in other embodiments, therapy system 10 may be used to deliver stimulation or therapeutic substances to the spinal cord or an occipital nerve for treatment of pain, the brain, or other areas of the nervous system, in which case, lead 14 or a catheter would be implanted proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders.

Therapy system 10 also may include a clinician programmer 26 and an intermediate device 28. Intermediate device 28 is a device that patient 16 may use to interact with IMD 12, and may be, for example, a patient therapy manager (PTM), i.e., a patient programming device. In one embodiment, intermediate device 28 may be a telemetry device as described in commonly-assigned U.S. Patent Application Serial No. 11/940,734, U.S. Patent Application Publication No. 2008/0140163 by Keacher et al., entitled, "TELEMETRY DEVICE FOR A MEDICAL DEVICE PROGRAMMER" which was filed on Nov. 15, 2007, and is incorporated herein by reference in its entirety. For example, intermediate device 28 may be a telemetry device comprising a housing, a first transceiver disposed within the housing and configured to transmit and receive information from an implantable medical device according to a first communication protocol, a second transceiver disposed within the housing and configured to transmit and receive information from a medical device programmer according to a second communication protocol, a user interface configured to receive input from a user, and a processor disposed within the housing and configured to generate a programming signal in accordance with the input from the user, where the first transceiver transmits the programming signal to the implantable medical device. The telemetry device may take a variety of forms, such as a key fob or the like, and may provide a limited user interface for programming relative to conventional clinician, or even patient, programming devices.

A clinician, caregiver, and/or other qualified individuals may use intermediate device 28 in addition to or instead of patient 16. Intermediate device 28 is typically a custom computing device with limited input/output capabilities and custom software that communicates with IMD 12. According to the present invention, intermediate device 28 may also be used as an intermediate security link between the IMD 12 and clinician programmer 26. As will be discussed in further detail below, this intermediate security link provides a layer of security and safety between clinician programmer 26 and IMD 12.

Clinician programmer 26 is a device that a clinician or other medical professionals may use to communicate with IMD 12. Clinician programmer 26 may perform advanced device setup and diagnostics and may optionally perform the programming functions of intermediate device 28 as well. Clinician programmer 26 communicates with IMD 12 via intermediate device 28, which provides as an intermediate security link between clinician programmer 26 and IMD 12. In this manner, clinician programmer 26 communicates directly with intermediate device 28, and intermediate device 28 communicates directly with IMD 12. Traditionally, clinician programmers have been capable of communicating directly with IMD 12. However, using intermediate device 28 as an intermediate security link between clinician programmer 26 and IMD 12 may be beneficial when clinician programmer 26 is not a custom computing device dedicated to programming IMD 12, but rather is, e.g., a general purpose computing device that may, e.g., be used to perform tasks unrelated to IMD 12. For example, clinician programmer 26 may be an off-the-shelf personal computer (PC).

Clinician programmer 26 may be a computing device that permits a clinician to program therapy for patient 16, e.g., using input keys and a display. For example, using clinician programmer 26, the clinician may specify parameters for use in delivery of therapy via IMD 12. Clinician programmer 26 communicates with intermediate device 28 which in turn communicates with IMD 12. In this manner, therapy parameters or other programming instructions may be downloaded to IMD 12 from clinician programmer 26. Optionally, operational or physiological data stored by IMD 12 may be uploaded to clinician programmer 26 via intermediate device 28. In this manner, a clinician or other medical professional may periodically interrogate IMD 12 to evaluate efficacy of the therapy delivered by IMD 12, and, if necessary, modify the therapy parameters. IMD 12 may also be interrogated via clinician programmer by way of intermediate device 28 to retrieve information stored within a memory of IMD 12, such as physiological parameter measurements taken by IMD 12 or a sensor coupled to IMD 12 or IMD 12 diagnostic data (e.g., electrode impedance measurements or a power level).

Intermediate device 28 may be a handheld computing device and may include a display and input keys to allow patient 16 to interact with intermediate device 28 and IMD 12. Intermediate device 28 may provide patient 16 with an interface for control of the therapy delivered by IMD 12, e.g., may be a patient programming device or PTM. For example, patient 16 may use intermediate device 28 to start, stop, or adjust therapy. In embodiments in which IMD 12 is an electrical stimulator, intermediate device 28 may permit patient 16 to adjust stimulation parameters such as duration, amplitude, pulse width, and pulse rate within an adjustment range specified by a clinician via clinician programmer 26 or select from a library of stored stimulation therapy programs.

Clinician programmer 26 and intermediate device 28 may communicate via cables, or a wireless communication link as shown in FIG. 1. For example, clinician programmer 26 and intermediate device 28 may communicate with each other using any of a variety of local wireless communication techniques, such as radio frequency (RF) communication according to the 802.11 or Bluetooth specification sets, infrared communication, e.g., according to the IrDA standard, or other standard or proprietary communication protocols. Additionally or alternatively, clinician programmer 26 and intermediate device 28 may communicate via a wired connection, such as via a serial communication or USB cable. Further, clinician programmer 26 may communicate with intermediate device 28 via remote telemetry techniques known in the art, communicating via a local area network (LAN), wide area network (WAN), public switched telephone network (PSTN), or cellular telephone network, for example. Intermediate device 28 and IMD 12 may communicate via a wireless communication link using RF telemetry techniques and standard or proprietary telemetry protocols, as is known in the art.

Figure 2:
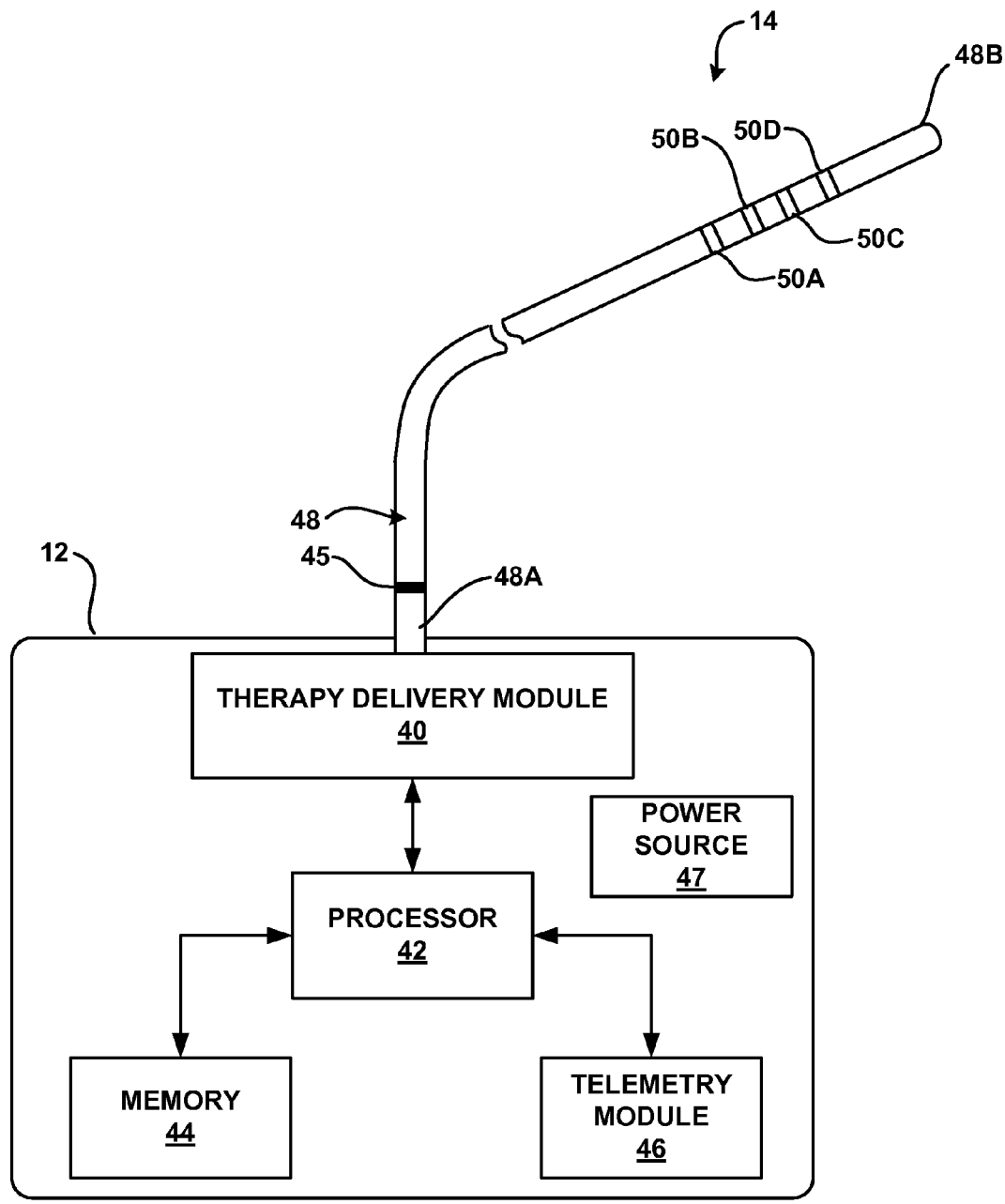
FIG. 2 is a schematic block diagram illustrating example components of the implantable medical device of FIG. 1 and an implantable lead.

FIG. 2 is a block diagram illustrating various components of IMD 12 and implantable lead 14. IMD 12 includes therapy delivery module 40, processor 42, memory 44, telemetry module 46, and power source 47. In some embodiments, IMD 12 may also include a sensing circuit (not shown in FIG. 2). Implantable lead 14 includes elongated lead body 48 extending between proximal end 48A and distal end 48B. Lead body 48 may be a cylindrical or may be a paddle-shaped (i.e., a "paddle" lead). Electrodes 50A, 50B, 50C, and 50D (collectively "electrodes 50") are disposed on lead body 48 adjacent to distal end 48B of lead body 48.

In some embodiments, electrodes 50 may be ring electrodes. In other embodiments, electrodes 50 may be segmented or partial ring electrodes, each of which extends along an arc less than 360 degrees (e.g., 90-120 degrees) around the periphery of lead body 48. In embodiments in which lead 14 is a paddle lead, electrodes 50 may extend along one side of lead body 48. The configuration, type, and number of electrodes 50 illustrated in FIG. 2 are merely exemplary.

Electrodes 50 extending around a portion of the circumference of lead body 48 or along one side of a paddle lead may be useful for providing an electrical stimulation field in a particular direction/targeting a particular therapy delivery site. For example, in applications involving electrical stimulation of a nerve proximate to the scalp of patient 16 (e.g., an occipital nerve), electrodes 50 may be disposed along lead body 48 such that the electrodes face toward the target nerve, or otherwise away from the scalp of patient 16. This may be an efficient use of stimulation because electrical stimulation of the scalp may not provide any or may provide minimal therapy to patient 16. In addition, the use of segmented or partial ring electrodes 50 may reduce the overall power delivered to electrodes 50 by IMD 12 because of the efficient delivery of stimulation to the target stimulation site by eliminating or minimizing the delivery of stimulation to unwanted or unnecessary regions within patient 16.

In embodiments in which electrodes 50 extend around a portion of the circumference of lead body 48 or along one side of a paddle lead, lead 14 may include one or more orientation markers 45 proximate to proximal end 14A that indicate the relative location of electrodes 50. Orientation marker 45 may be a printed marking on lead body 48, an indentation in lead body 48, a radiographic marker, or another type of marker that is visible or otherwise detectable (e.g., detectable by a radiographic device) by a clinician. Orientation marker 45 may help a clinician properly orient lead 14 such that electrodes 50 face the desired direction within patient 16. For example, orientation marker 45 may also extend around the same portion of the circumference of lead body 48 or along the side of the paddle lead as electrodes 50. In this way, orientation marker 45 faces the same direction as electrodes, thus indicating the orientation of electrodes 50 to the clinician. When the clinician implants lead 14 in patient 16, orientation marker 45 may remain visible to the clinician.

IMD 12 delivers stimulation therapy via electrodes 50 of lead 14. In particular, electrodes 50 are electrically coupled to a therapy delivery module 40 of IMD 12 via conductors within lead body 48. In one embodiment, an implantable signal generator or other stimulation circuitry within therapy delivery module 40 delivers electrical signals (e.g., pulses or substantially continuous-time signals, such as sinusoidal signals) to target stimulation site 18 (FIG. 1) via at least some of electrodes 50 under the control of processor 42. The implantable signal generator, as well as processor 42, may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The electrical signals may be delivered from therapy delivery module 40 to electrodes 50 via a switch matrix and conductors carried by lead 14 and electrically coupled to respective electrodes 50. The coupling via switch matrix may be controlled by processor 42.

Processor 42 may include a microprocessor, a controller, a digital signal processor (DSP), an application specific integrated circuit (ASIC), a field programmable gate array (FPGA), discrete logic circuitry, or the like. Processor 42 controls the signal generator within therapy delivery module 40 to deliver neurostimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the neurostimulation signals via selected subsets of electrodes 50 with selected polarities, e.g., through control of the switch matrix. For example, electrodes 50 may be combined in various bipolar or multi-polar combinations to deliver stimulation energy to selected sites, such as nerve sites adjacent the spinal column, pelvic floor nerve sites, or cranial nerve sites. Processor 42 may also control therapy delivery module 40 to deliver each signal according to a different program, thereby interleaving programs to simultaneously treat different symptoms or provide a combined therapeutic effect.

Memory 44 of IMD 12 may include any volatile or non-volatile media, such as a random access memory (RAM), read only memory (ROM), non-volatile random access memory (NVRAM), electrically erasable programmable read only memory (EEPROM), flash memory, and the like. In some embodiments, memory 44 of IMD 12 may store multiple sets of stimulation parameters, e.g., programs, that are available to be selected by clinician programmer 26 (via intermediate device 28) or intermediate device 28 (FIG. 1) for delivery of neurostimulation therapy. Further the programs may be loaded or modified in memory 44 by clinician programmer 26 (via intermediate device 28) or intermediate device 28. Memory 44 also stores program instructions that, when executed by processor 42, cause IMD 12 to deliver neurostimulation therapy. Accordingly, computer-readable media storing instructions may be provided to cause processor 42 to provide functionality as described herein.

Processor 42 controls telemetry module 46 to exchange information with intermediate device 28 for the aforementioned purposes by wireless telemetry. For example, processor 42 may control telemetry module 46 to communicate indirectly with clinician programmer 26 through intermediate device 26, which enables IMD 12 to receive programming instructions or to load, modify or select a program stored within memory 44 based on indirect communication from clinician programmer 26 via intermediate device 28. In addition, IMD 12 may receive instructions from clinician programmer 26 or intermediate device 28 requesting diagnostic information, such as diagnostic information about the performance of IMD 12 (e.g., remaining battery life or electrode impedance) or patient data stored within a memory of IMD 12 (e.g., physiological parameter measurements).

Figure 3:
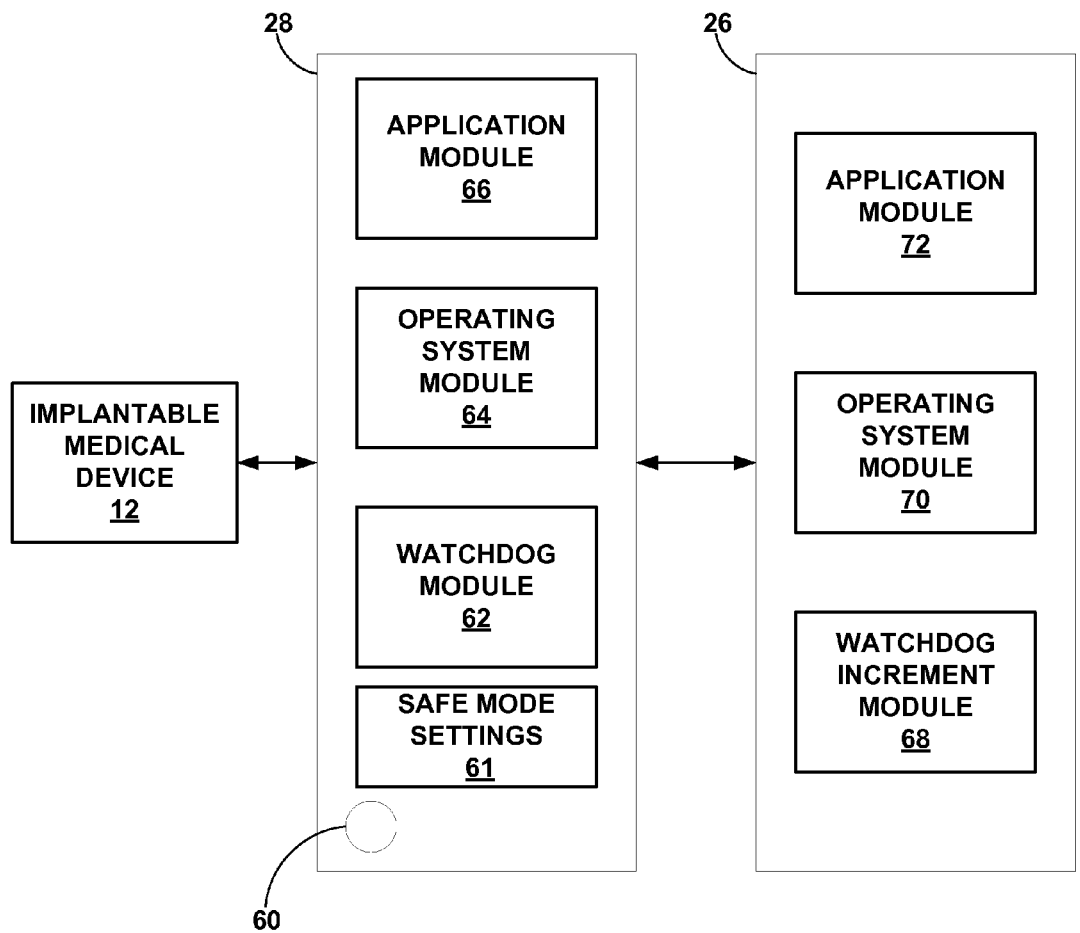
FIG. 3 illustrates one embodiment of a system that includes an intermediate device as an intermediate security link between a clinician programmer and an implantable medical device, where the intermediate device includes a watchdog module.

FIG. 3 illustrates one embodiment of a system in which intermediate device 28 provides an intermediate security link between clinician programmer 26 and IMD 12. As the medical industry becomes more technology oriented, computing devices tend to have an increasingly important role. In general, a computing device includes software coupled with a processor (e.g., a microprocessor). In some embodiments, the software coupled with the processor may comprise instructions defining an operating environment that presents a graphical user interface to a user.

Traditionally, clinician programmers have been custom computing devices dedicated to programming implantable medical devices. More specifically, a clinician programmer has traditionally been a dedicated hardware device with dedicated software for programming of the implantable medical device. Although the software used for programming implantable medical devices is typically unique to the type of medical device being programmed, the hardware used is often very similar to that which already exists for other purposes within the medical industry (e.g., devices in an examination or operating room).

According to the invention, clinician programmer 26 may be a computing device that already exists for other functions (e.g., within a hospital or physician's office or outside of the medical industry). In this manner, customized software may be run on standard, non-dedicated computing devices (e.g., desktop personal computers, laptops, and/or tablet computers). Allowing clinician programmer 26 to use computing devices that already exist for other functions (i.e., other than dedicated medical device programmers) may save space within a clinician's office and may be a more efficient use of resources, e.g., money.

However, modern computing devices used in the medical industry, such as computers, are typically networked and run common desktop operating systems. These computing devices are prone to computer viruses and other security threats. An intermediate security link between clinician programmer 26 and IMD 12 may help reduce the risks of using a standard, non-dedicated computing device as the hardware component of clinician programmer 26. The use of a standard, non-dedicated computing device (e.g., a desktop, laptop, or tablet) running a commercial operating system (e.g., Windows XP or Vista made available by Microsoft Corporation of Redmond, Wash.) may introduce hazards and risks into the integrity of the communication between IMD 12 and clinician programmer 26. These risks include possible conflicts for resources with other programs within the computing device, effects of viruses or other corruption of the computing device applications, or other disruptions of the expected operation of the computing device. The worst case effect of these disruptions may be transmission of repeated, spurious, or erroneous commands to IMD 12, which may result in unintended changes to the therapy delivered to patient 16 by IMD 12.

To help reduce the risk of unintended changes to the therapy delivered by IMD 12, a safe mode may be defined for IMD 12 and IMD 12 may revert to the safe mode in certain circumstances. The safe mode is a set of parameters that is known to provide a safe and comfortable therapy to patient 16 from IMD 12. For example, the safe mode for an implanted neurostimulator may be to set the stimulation amplitude to 0 volts. This would effectively turn off the stimulation and remove any undesirable side effects of the therapy.

For some therapies and patients, however, turning off the therapy may not be safe or comfortable. In the example of an implanted neurostimulator, the safe mode for patient 16 may be a specific combination of therapy parameters that yield a safe and comfortable therapy setting. In some embodiments, the safe mode is a preconfigured setting or a rollback to a last or last-known safe and comfortable therapy state. For an implantable drug delivery device, the safe mode setting may involve a user-predefined rate which takes into account the possibilities of drug concentration change, tube-set, and/or other variables.

In some embodiments, the safe mode may be defined by allowing patient 16, a clinician, a caregiver, or another qualified individual to save one or more safe therapy configurations that provide patient 16 with safe and comfortable therapy. In other embodiments, IMD 12 may determine the therapy parameters of the safe mode, such as by implementing an algorithm that configures the safe mode based on a last known therapy program, which includes one or more therapy parameters, that yielded safe and comfortable therapy to patient 16. Patient 16, a clinician, a caregiver, or another qualified individual may have the ability to rollback to any of the safe mode configurations for IMD 12 as desired. For example, as described in further detail below, patient 16 may provide input indicating a desire to revert IMD 12 to a safe mode, where the input may be provided via safe mode button 60 (FIGS. 1 and 3) of intermediate device 28.

The safe mode may be patient, therapy, and/or clinician specific. In some embodiments, one safe mode configuration may be used for all patients who receive a certain type of treatment. For example, the safe mode for a drug delivery device may involve suspending drug delivery. In this embodiment, the patient may be alerted when IMD 12 enters safe mode and may be instructed to take oral medications until therapy is restored. In other embodiments, a clinician may use a specific safe mode for all patients. For example, the safe mode may be set to fifty percent of a last-known therapy. In yet other embodiments, the safe mode may be specific to the individual patient 16 and customizable based on the needs and symptoms of patient 16.

A safe mode button 60 (also shown in FIG. 1) may be included on intermediate device 28 to provide immediate programming of IMD 12 to a defined safe mode. The safe mode settings may be saved within safe mode module 61 of intermediate device 28, which may include any volatile or non-volatile media, such as a RAM, ROM, NVRAM, EEPROM, flash memory, and the like to store the safe mode settings for IMD 12. Alternatively, the settings for the safe mode of IMD 12 may be stored in IMD 12, and intermediate device 28 may provide instructions to IMD 12 to access and implement the stored safe mode setting, rather than sending the actual safe mode settings themselves.

If the safe mode configuration is stored within IMD 12, a universal safe mode command may be used to program IMD 12 to enter the safe mode. A universal safe mode command may be compatible with at least two different types of IMDs designed and/or manufactured by a particular manufacturer. For example, all electrical stimulators produced by Medtronic, Inc. of Minneapolis, Minn. may be programmed to enter a safe mode in response to receiving the universal command. In other embodiments, the universal command may be compatible with two or more IMDs that were designed and/or manufactured by different manufacturers. For example, the universal command may be understood by IMDs designed and/or manufactured by any manufacturer that chooses to comply with a protocol for communicating the universal command. In some embodiments, the universal command may use government regulated standard communication bands and/or protocols (e.g., MICS or MEDS bands).

A universal command may be particularly useful in emergency situations in which an emergency room clinician or other medical professional may have no or little information about IMD 12. A universal safe mode command may allow the clinician to activate the safe mode using a universal programmer programmed with the universal safe mode command if the patient's programmer is not present and the clinician does not have access to a clinician programmer 26 that is specifically configured to communicate with IMD 12.

Activation of safe mode button 60 may suspend processing of commands sent from clinician programmer 26 to intermediate device 28 pending a reset action by patient 16 or a clinician via intermediate device 28. Safe mode button 60 may serve as a viable mechanism to mitigate hazards associated with unintended programming coming from clinician programmer 26 by allowing patient 16 to restore IMD 12 to a known safe mode state. Safe mode button 60 is not limited to a physical button, and may be activated by any user input media. For example, safe mode button 60 may be a push button, soft-key, voice-activated command, activated by physical interaction, magnetically triggered, or activated upon password authentication. Safe mode button 60 may be implemented alone or in combination with other safety features (e.g., a watchdog (FIG. 3), system mediator 80 (FIG. 4), or a remote user interface (FIG. 5). In some embodiments, safe mode may also be activated automatically, e.g., by a watchdog or system mediator 80, rather than being manually activated via safe mode button 60.

In embodiments in which IMD 12 stores the safe mode setting, IMD 12 may automatically revert to safe mode under certain conditions. For example, if IMD 12 is expecting a stay-alive and/or end command from a patient programmer and does not receive the command after a period of time, IMD 12 may program itself to go into safe mode. This may prevent IMD 12 from being left in an unsafe state if the communication between the patient programmer and IMD 12 is interrupted during programming of IMD 12.

One embodiment of the intermediate security link between clinician programmer 26 and IMD 12 includes a system watchdog, as illustrated in FIG. 3. In the illustrated embodiment, the system watchdog comprises system watchdog module 62 of intermediate device 28 and watchdog increment module 68 of clinician programmer 26. Intermediate device 28 and clinician programmer 26 further comprise application modules 66 and 72 and operating system modules 64 and 70, respectively. Application modules 66 and 72 may contain software applications that may be run on intermediate device 28 and clinician programmer 26 and operating system modules 64 and 70 may contain software defining the operation systems (e.g., Windows Vista or a custom operating system) which intermediate device 28 and clinician programmer 26, respectively, use to run the software applications. Application modules 66 and 72, operating system modules 64 and 70, system watchdog module 62, and system watchdog increment module 68 may each comprise software that may be executed by a processor, which may be may include a microprocessor, a controller, a DSP, an ASIC, an FPGA, discrete logic circuitry, or the like. A separate processor may be associated with each of the modules 62, 64, 66 of intermediate device 28 or two or more of the modules 62, 64, 66 may be controlled by a common processor. The software may be stored within separate or common memory of the intermediate device. The memory may include any volatile or non-volatile media, such as a RAM, ROM, NVRAM, EEPROM, flash memory, and the like. Similarly, a separate processor may be associated with each of the modules 68, 70, 72 of clinician programmer 26 or two or more of the modules may be controlled by a common processor.

System watchdog module 62 of intermediate device 28 may indirectly verify that information transmitted from clinician programmer 26 to intermediate device 28, e.g., a programming command for IMD 12, is valid without analyzing the logical validity of the content of the information. For example, system watchdog module 62 may comprise a software task that runs on intermediate device 28 to monitor the behavior of clinician programmer 26. More specifically, in one embodiment, system watchdog module 62 expects to periodically receive a defined signal, such as elements of a signature, from clinician programmer 26 at predetermined intervals during a programming session (e.g., while clinician programmer 26 is sending commands to intermediate device 28). In this manner, intermediate device 28 (the more secure device) monitors clinician programmer 26 (the less secure device). The signature or other signal transmitted from clinician programmer 26 to intermediate device 28 may be, for example, a series of sequential numbers or a predefined pattern of numbers.

Watchdog increment module 68 on clinician programmer 26 may deliver the defined signature from clinician programmer 26 to intermediate device 28 at predetermined time intervals. Described in further detail below, the watchdog increment module 68 may be reset by rebooting clinician programmer 26 or by any other suitable means.

Watchdog module 62 may maintain a timer, and reset the timer in response to receiving each element of the signature. Expiration of the watchdog timer may involve either counting up to or down from a predetermined value related to the time intervals at which the clinician programmer sends the signature. The signature may include a completion indicator that notifies intermediate device 28 when clinician programmer 26 has successfully completed sending instructions to intermediate device 28. In other embodiments, the completion indicator may be sent separately from the signature to notify intermediate device 28 when clinician programmer 26 has successfully completed sending instructions to intermediate device 28.

If for any reason, the transmission of the defined signature from clinician programmer 26 to intermediate device 28 is interrupted during a programming session, intermediate device 28 may stop forwarding instructions from clinician programmer 26 and change the therapy delivered by IMD 12 to the safe mode until the watchdog is reset. In one embodiment, the interruption in the transmission of the defined signature is indicated by expiration of the timer maintained by watchdog module 62 (e.g., between the start of the transmission of the defined signature and the transmission of the completion indicator). More specifically, if intermediate device 28 does not receive the next element in the sequence of the signature before the timer expires, intermediate device 28 may change the therapy delivered by IMD 12 to the safe mode.

For example, if intermediate device 28 does not receive any signals from watchdog increment module 68 of clinician programmer 26 before the timer elapses, which may indicate that the clinician programmer 26 has become CPU bound (e.g., clinician programmer 26 is prevented from successfully performing an operation due to the programming application receiving insufficient processing resources as a result of another unrelated application monopolizing them), intermediate device 28 may change the therapy delivered by IMD 12 to the safe mode. As another example, intermediate device 28 may also change the therapy delivered by IMD 12 to the safe mode if an incorrect element in the sequence of the signature is received. For example, if intermediate device 28 receives an element of the signature multiple times, which may indicate that clinician programmer 26 in stuck in an infinite loop, intermediate device 28 may change the therapy delivered by IMD 12 to the safe mode.

To ensure that the watchdog is not incremented unless all other critical tasks for sending valid information to intermediate device 28 have been run to completion, the task that increments the watchdog, i.e., the watchdog increment task, may be the lowest priority critical task running on clinician programmer 26. In some embodiments, the watchdog increment task is the lowest priority task running on clinician programmer 26 overall. The watchdog increment task may be set as a low priority task to help prevent the defined signature from continuing to be transmitted if clinician programmer 26 has become CPU bound or encountered any other problem that may inhibit transmission of commands to intermediate device 28. Additionally, watchdog increment module 68 may monitor other operations of clinician programmer 26 to help ensure that no process inadvertently permanently disables the watchdog increment task and/or enables the watchdog increment task under inappropriate conditions. This monitoring may be coupled to the watchdog increment task and performed as a low priority task.

For example, if an application task is stuck in an infinite loop that is mistakenly sending the same telemetry message to intermediate device 28, the watchdog increment task on clinician programmer 26 would never run. After a predefined amount of time during which watchdog module 62 of intermediate device 28 does not receive an element of the defined signature from watchdog increment module 68 of clinician programmer 26, watchdog module 62 may instruct intermediate device 28 to program IMD 12 to go into the safe mode and may refuse further commands from clinician programmer 26 until watchdog increment module 68 is reset.

As mentioned previously, watchdog increment module 68 may be reset by rebooting clinician programmer 26. Additionally, if clinician programmer 26 recovers from a problem, it may automatically reset watchdog increment module 68 and send a reset indication message to intermediate device 28. Alternatively, after transmission of the defined signature has been interrupted, intermediate device 28 may send a reset command to clinician programmer 26 to attempt to reset watchdog increment module 68. If successful, clinician programmer 26 may send a reset indication message to intermediate device 28. As an additional alternative, clinician programmer 26 and/or intermediate device 28 may include a button or other means that may be activated by a user to reset the watchdog function.

Figure 4:
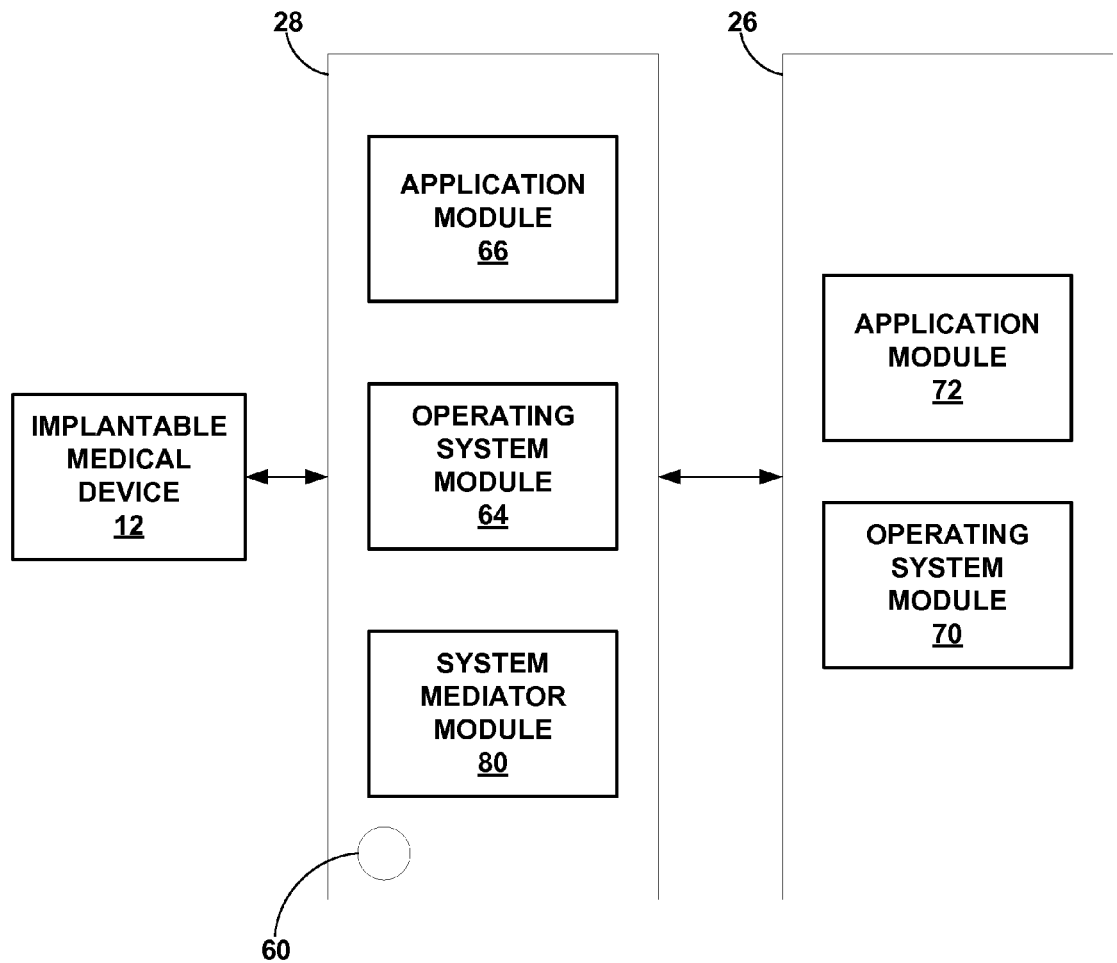
FIG. 4 illustrates an embodiment of a system in which an intermediate device includes a system mediator to verify and validate programming instructions received from a clinician programmer.
Figure 5:
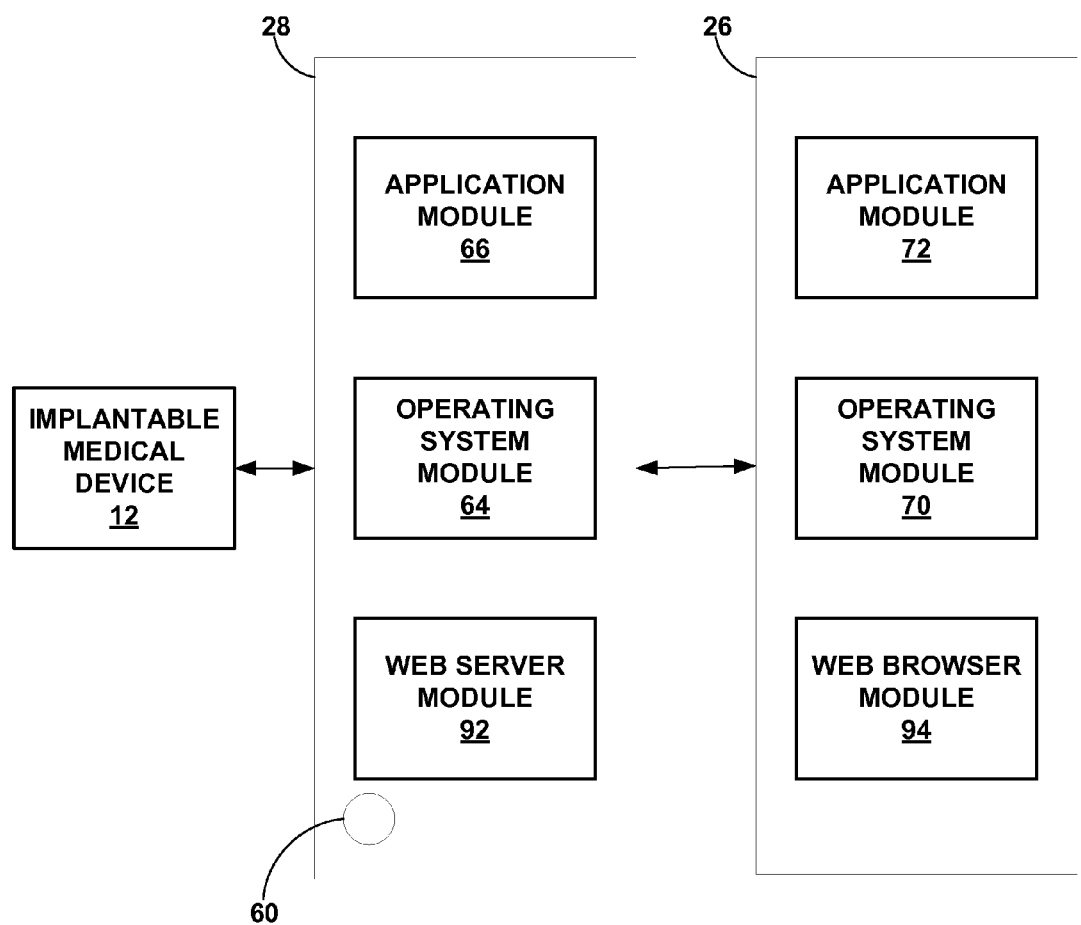
FIG. 5 illustrates an embodiment in which the clinician programmer acts as a user input terminal that accesses clinician programming function on an intermediate device.

In another embodiment, as illustrated in FIG. 4, intermediate device 28 includes a system mediator module 80 to verify and validate information received from clinician programmer 26, System mediator 80 may be provided in addition to or as an alternative to the watchdog module 62 described with respect to FIG. 3, Intermediate device 28 and clinician programmer 26 may include application modules 66 and 72 and operating system modules 64 and 70, respectively, Application modules 66 and 72 and operating system modules 64 and 70 may each comprise software that may be executed by a processor. Application modules 66 and 72 may contain software applications that may be run on intermediate device 28 and clinician programmer 26 and operating system modules 64 and 70 may contain software defining the operation systems (e.g., Windows Vista or a custom operating system) which intermediate device 28 and clinician programmer 26 use to run the software applications. In addition, intermediate device 28 may also include a safe mode button 60 and safe mode setting module 61 (shown in FIG. 3) to store the safe mode settings of IMD 12 or instructions for programming IMD 12 to enter into a safe mode.

System mediator 80 may be a dedicated task on intermediate device 28 that provides a secure link between clinician programmer 26 and IMD 12 by verifying and validating the content of programming instructions being transmitted from clinician programmer 26 to intermediate device 28. System mediator 80 may be an application layer filter that is able to discern between logically valid programming instructions and erroneous programming instructions. In this manner, system mediator 80 provides as an intermediate security link between intermediate device 28 and clinician programmer 26.

System mediator 80 of intermediate device 28 may be able to distinguish the difference between logically valid information and logically invalid information received from clinician programmer 26. For example, if clinician programmer 26 tries to program IMD 12 with extreme combinations of parameters that are obviously not part of intended therapy (e.g., far removed from the last known therapy parameter that yielded safe therapy delivery to patient 16), intermediate device 28 will recognize these invalid parameters and will not send the programming instructions to IMD 12 or may require confirmation via user interaction with the PTM before sending them. System mediator 80 may do reasonability and/or consistency checks, such as determining if too little or too much time has passed between commands, evaluating sequence numbering, comparing therapy parameter values to device and/or patient specific acceptable ranges, comparing dosage values set forth by the programming instructions to labeling instructions for a medication, identifying a mismatch of commands to the device (e.g., stimulation instructions sent to a drug delivery device), recognizing an invalid pattern of commands (e.g., a repeated loop), evaluating the environmental context of the commands (e.g., signal strength), identifying contradictions to previously sent commands (e.g., drug reservoir is empty after refilling drug reservoir), and/or any number of other checks, to judge the validity of information sent from clinician programmer 26 and act upon invalid commands in an appropriate manner.

In some embodiments, system mediator 80 may receive a first programming command and decide to wait to receive one or more additional programming commands before determining the validity of the first command. For example, system mediator 80 may determine that the first programming command is only valid if followed by a certain type of programming command and may wait to determine the validity of the first command until a second command is received. This may also be useful in addressing interruptions in the transmission of programming commands from clinician programmer 26 to intermediate device 28. For example, if system mediator 80 expects to receive more programming commands in a programming sequence from clinician programmer 26, system mediator 80 may wait to determine the validity of each of the programming commands until all of the commands in the sequence have been received by system mediator 80. In such manner, interruptions in the transmission of programming commands from clinician programmer 26 to intermediate device 28 may not result in interruptions in the transmission of programming commands from intermediate device 28 to IMD 12.

In response to determining that the content of the programming instructions/commands from clinician programmer 26 are invalid, system mediator 80 may cause IMD 12 to revert to a safe mode and/or system mediator 80 may refuse commands from clinician programmer 26 until clinician programmer 26 is reset.

Clinician programmer 26 may be reset, for example, by rebooting and/or activation of a reset button that initiates the reset. Additionally or alternatively, clinician programmer 26 may automatically reset upon recovering from a problem and/or intermediate device 28 may attempt to initiate the reset of clinician programmer 26 by sending a reset signal to clinician programmer 26. In some embodiments, clinician programmer 26 sends a reset indication message to intermediate device 28 that notifies intermediate device 28 when clinician programmer 26 has been reset.

Clinician programmer 26 may not format programming instructions sent to intermediate device 28 in the same format that the programming instructions are sent from intermediate device 28 to IMD 12. For example, clinician programmer 26 may send an instruction to intermediate device 28 that indicates a desired outcome for IMD 12, and the request command may be approved or denied by system mediator 80. The request command may be in a more general format than the commands sent from intermediate device 28 to IMD 12 and may indicate a batching of telemetry commands. System mediator 80 or a processor of intermediate device 28 may then "translate" the instructions from clinician programmer 26 into a format that IMD 12 will understand and accept. In other embodiments, the same message format may be used for messages sent from clinician programmer 26 to intermediate device 28 and message sent from intermediate device 28 to IMD 12.

System mediator 80 may require patient 16 to validate certain requests sent to intermediate device 28 from clinician programmer 26 using a user interface provided on intermediate device 28. For example, system mediator 80 may prompt patient 16 to validate a request via a command window on intermediate device 28, and patient 16 may be required to press a validation button before intermediate device 28 allows the request to be transmitted to IMD 12. Validation from patient 16 may be useful if clinician programmer 26 is requesting changes to parameters that are significantly different than the parameters typically set for IMD 12. For example, if clinician programmer 26 requests changes to therapy parameters that will cause IMD 12 to deliver therapy significantly different from the therapy that IMD 12 typically delivers to patient 16, validation from patient 16 may be useful. System mediator 80 may implement a software algorithm to keep track of normal versus abnormal therapy for a given patient 16. System mediator 80 may also keep track of device-specific ranges of acceptable therapy parameter values, patient-specific ranges of acceptable therapy parameter values drug labeling instructions, and/or other therapy information. In the event that abnormal therapy is being requested, intermediate device 28 may request additional verification from patient 16.

IMD 12 may include system mediator 80 in addition to or instead of intermediate device 28. For example, in some embodiments, the functionality of system mediator 80 may be split between both IMD 12 and intermediate device 28, while in other embodiments, system mediator 80 is positioned exclusively within IMD 12. In such an embodiment, intermediate device 28 may merely transmit information from clinician programmer 26 to IMD 12 without checking the logical validity of the content of the information. However, intermediate device 28 may still include watchdog module 62 to determine whether the programming command from clinician programmer 26 is valid without analyzing the logical validity of the content of the information.

Similarly, regardless of whether the functions of system mediator 80 may be performed by intermediate device 28 or IMD 12, the upper and lower bounds for reasonable checks of the therapy parameters of the programming instructions and the bounds or other thresholds for determining whether the programming instructions include therapy parameters for normal or abnormal therapy may be stored in intermediate device 28 and/or IMD 12. For example, in some embodiments IMD 12 may receive programming instructions from a computing device (e.g., intermediate device 28, a patient programming device, and/or a clinician programming device), analyze the programming instructions, determine whether the content of the instructions is logically valid based on the analysis, and control a therapy delivered from the implantable medical device based on the determination, i.e., if the content of the instructions is logically valid.

In another embodiment, as illustrated in FIG. 5, clinician programmer 26 functions as a user input terminal for accessing control functions stored within intermediate device 28. In this manner, clinician programmer 26 provides a remote interface for intermediate device 28. The remote user interface and intermediate device 28 may be linked using any suitable means, such as a cable, USB connection, wireless network or via an internet network. In one embodiment, substantially all control functions for clinician programmer 26 may be stored within intermediate device 28, which provides an intermediate security link between clinician programmer 26 and IMD 12. The remote user interface may be implemented alone or in combination with safe mode button 60, other safe mode implementations, a watchdog module 62 (FIG. 3), and/or system mediator module 80 (FIG. 4).

Applications module 66 of intermediate device 28 may include a plurality of instructions for IMD 12. The instructions may include both programming instructions to program one or more therapy parameters into IMD 12 or instruct IMD 12 to deliver therapy according to another program and diagnostic instructions, which may be requests for receiving information stored within memory 44 of IMD 12. The instructions may be presented to a user via the user input terminal, and the user may provide input indicating one or more of the instructions to deliver to IMD 12. In some embodiments, the user input is provided via a user interface (e.g., a touch screen, buttons, keyboard, etc.) of the user input terminal and transmitted to the intermediate computing device (e.g., via a wired or wireless signal). In other embodiments, the user input is provided via a user interface of intermediate device 28.

As previously described, in some embodiments, clinician programmer 26 may act as a user input terminal that access control functions within applications module 66 of intermediate device 28. The control functions that clinician programmer 26 may access within intermediate device 28 may include, for example, one or more selectable input therapy parameters for programming IMD 12. In the case of an electrical stimulator, the input therapy parameters define an electrode pattern (i.e., the pattern of anodes and cathodes), stimulation amplitude, frequency, and so forth with which IMD 12 delivers electrical stimulation therapy to patient 16. In the case of a fluid delivery device, the input therapy parameters may define a concentration of a fluid that the fluid delivery device delivers to patient 16, frequency of fluid delivery, size of a bolus, and so forth.

In embodiments in which intermediate device 28 couples to a remote user interface, the remote user interface may provide a patient, clinician or other medical professional access to advanced features that are not available via direct manipulation of intermediate device 28. For example, patient 16 may access patient programming type features through direct interaction with intermediate device 28. Clinician programming type features may be stored on intermediate device 28, such as in applications module 66, but may only be accessible through the remote user interface used by clinician programmer 26. Clinician programming type features may include advanced device setup and diagnostic capabilities. Additionally, patient programming type features may optionally be accessed via clinician programmer 26 and may include basic programming capabilities. In this manner, intermediate device 28 may provide direct access to a subset of programming capabilities accessible via clinician programmer 26.

In another embodiment, patient programming type features and clinician programming type features may both only be accessible using a remote user interface. In this manner, programming functions for IMD 12 may not be accessed through direct manipulation of intermediate device 28. Instead, intermediate device 28 may contain control functions for programming IMD 12 and may allow patient 16, a clinician, and/or other qualified individuals to access the control functions through one or more remote user interfaces.

In one embodiment, clinician programmer 26 provides a display for presenting information from application module 66, which runs on intermediate device 28. Application module 66 of intermediate device 28 may include the programming applications traditionally implemented by clinician programmer 26 (e.g., control functions for clinician programmer 26). The programming applications for clinician programmer 26 stored in applications module 66 may include the control functions typically available for clinician programmer 26 described above. The programming applications stored within intermediate device 28 may include, for example, programming instructions to programming therapy parameters of IMD 12, download patient data (e.g., physiological parameter values recorded by IMD 12, such as blood pressure, electrical activity, core body temperature, ECG data, etc.) from IMD 12, download IMD 12 diagnostic information from IMD 12, and so forth. In this way, a user may interface with clinician programmer applications that are stored within applications module 66 of intermediate device 28 with the aid of the display of clinician programmer 26. Information that is communicated from intermediate device 28 to clinician programmer 26 may pertain to graphics and/or other indicators that may be displayed on clinician programmer 26.

In some embodiments, in addition to displaying information to a user, clinician programmer 26 functions as a user input terminal that is configured to receive input from a user. Information communicated from clinician programmer 26 to intermediate device 28 may pertain to inputs selected by a user via clinician programmer 26. A user, such as a clinician or other medical professional, may provide input via a touch screen, keyboard, buttons, a peripheral pointing device or other appropriate input means available on clinician programmer 26. Alternatively, clinician programmer 26 merely provides a display for presenting information from intermediate device 28, and a user provides input via a user interface on intermediate device 28. The user interface of intermediate device 28 may include, for example, a touch screen, keyboard, buttons, a peripheral pointing device or other appropriate input means.

In another embodiment, a user interface (including a display) provided on intermediate device 28 may be mirrored to a separate computing device, such as clinician programmer 26, which, as described above, may include an undedicated personal computer. Mirroring the user interface, e.g., the display, provided by intermediate device 28 to the separate computing device provides patient 16, a clinician, and/or another qualified individual with the option to use the separate computing device as a user interface for intermediate device 28. For example, patient 16 may use a separate computing device with a larger screen than intermediate device 28 as a user interface for the intermediate device. This may be beneficial to patients with visual and/or tactile impairments or to implement interfaces that would be too complex when used on the intermediate device display.

In another embodiment, intermediate device 28 includes web server module 92 and clinician programmer 26 includes web browser module 94 to facilitate communication between intermediate device 28 and clinician programmer 26. Intermediate device 28 and clinician programmer 26 comprise application modules 66 and 72 and operating system modules 64 and 70, respectively. Application modules 66 and 72, operating system modules 64 and 70, web server module 92, and web browser module 94 may each comprise software that may be executed by a processor. Application module 72 of clinician programmer 26 may comprise non-programming applications that run on clinician programmer 26. All programming functions of clinician programmer 26 may be confined to web browser module 94 of clinician programmer 26. As with the embodiments discussed above, in some embodiments, intermediate device 28 includes a safe mode button 60 that is coupled to a safe mode setting module that stores the safe mode settings for IMD 12, or alternatively, the settings may be stored within IMD 12.

Web server module 92 may include software, hardware or a combination of software and hardware, that is configured to accept requests from web browser module 94, which may also include a combination of software, hardware or a combination of software and hardware. For example, a user may input a request to access programming applications via web browser module 94 of clinician programmer 26. As another example, the user may input a request that indicates a specific therapy parameter for implementation by IMD 12 (i.e., the user may request a programming instruction be sent to IMD 12) via web browser module 94. The inputs may be provided to web browser module 94 via a user interface of clinician programmer 26. The requests provided to web server module 92 may substantially conform to the hypertext transfer protocol (HTTP).

Upon receiving the request from web browser module 94, web server module 92 may respond to web browser module 94, such as by providing information that defines a graphical display to present on a display of clinician programmer 26 via web browser module 94. The graphical display may provide an interface with which the user may provide further requests to web server module 92. As another example, if the user provides input to web server module 92 that requests a programming instruction be sent to IMD 12, web server module 92 provide confirmation to web browser module 94 that a programming instruction was successfully or unsuccessfully transmitted to IMD 12.

In yet another embodiment, clinician programmer 26 acts as a user terminal that provides access to a client server. Information that is communicated from intermediate device 28 to clinician programmer 26 may be limited to graphics and other indicators that may be displayed on clinician programmer 26. Information communicated from clinician programmer 26 to intermediate device 28 may be limited to display output and inputs selected by a user via clinician programmer 26 (e.g., via a touch screen, mouse, and/or keyboard). In this embodiment, intermediate device 28 may function as a client server that may be accessed by clinician programmer 26. In this embodiment, the interface between clinician programmer 26 and intermediate device 28 may be similar to terminal server programs, such as Virtual Network Computing, Windows Remote Desktop®, and Unix/Linux X terminal sessions.

In the embodiment in which clinician programmer 26 acts as a user terminal for accessing a client server (i.e., intermediate device 28), clinician programmer 26 may include a display that presents a graphical user interface that remotely controls features of intermediate device 28. For example, a user may remotely access applications module 66 of intermediate device 28 via clinician programmer 28. In one embodiment, inputs (e.g., via a keyboard or a peripheral pointing device, such as a mouse) provided to clinician programmer 26 during a remote access session are transmitted to intermediate device 28. The remote access may be gained through any suitable connection between intermediate device 28 and clinician programmer 26, such as a cabled connection, via wireless communication, USB connection, a LAN, WAN, via an internet connection, and so forth. In this embodiment as well as many of the other embodiments discussed herein, intermediate device 28 may request information from the user to verify the identity of the user. For example, the user may be provided with a user name and password that the user may input to intermediate device 28 in order to gain remote access to programming features of applications module 66 of intermediate device 28.

Various embodiments of the invention have been described. These and other embodiments are within the scope of the following claims.

The invention claimed is:

1. A method comprising:
receiving programming instructions for a medical device from a computing device, wherein the programming instructions comprise a first set of programming instructions and a second set of programming instructions;
analyzing a content of the first set of programming instructions;
determining whether the content of the first set of programming instructions is logically valid;
if the content of the first set of programming instructions is not logically valid, refusing further receipt of the second set of programming instructions from the computing device until an indication that the computing device has been reset is received; and
transmitting the first set of programming instructions to the medical device if the content of the first set of programming instructions is logically valid.

2. The method of claim 1, wherein receiving programming instructions from the computing device comprises receiving programming instructions at an intermediate computing device, and wherein analyzing the content of the first set of programming instructions comprises analyzing the content of the first set of programming instructions at the intermediate computing device.

3. The method of claim 2, wherein transmitting the first set of programming instructions to the medical device if the content of the first set of programming instructions is logically valid comprises transmitting the first set of programming instructions from the intermediate computing device to the medical device if the content of the first set of programming instructions is logically valid.

4. The method of claim 1, wherein analyzing the content of the first set of programming instructions comprises analyzing the content of the first set of programming instructions at the medical device.

5. The method of claim 1, wherein the computing device comprises at least one of an intermediate computing device, a patient programming device, or a clinician programmer.

6. The method of claim 1, further comprising placing the medical device in a known safe mode if the content of the first set of programming instructions is not logically valid.

7. The method of claim 1, wherein analyzing the content of the first set of programming instructions comprises comparing a therapy parameter value of the first set of programming instructions to at least one of a device-specific range of acceptable therapy parameter values, a patient-specific range of acceptable therapy parameter values, or medication dosage instructions.

8. The method of claim 7, wherein at least one of the device-specific range, the patient-specific range or the medication dosage instructions is stored within at least one of the medical device or an intermediate computing device.

9. The method of claim 1, wherein receiving programming instructions from the computing device comprises receiving the programming instructions during the course of a programming session between the computing device and the medical device, the method further comprising:
periodically receiving a defined signal from the computing device during the course of the programming session;
transmitting the first set of programming instructions to the medical device if the content of the programming instructions is logically valid; and
transmitting alternative instructions to the medical device instead of the first set of programming instructions in response to an interruption in transmission of the defined signal.

10. The method of claim 1, further comprising prompting a user to validate the content of the first set of programming instructions if the content of the first set of programming instructions is not logically valid.

11. A system comprising:
a computing device; and
a mediator module that is configured to:
receive programming instructions for a medical device from the computing device, wherein the programming instructions comprise a first set of programming instructions and a second set of programming instructions,
analyze a content of the first set of programming instructions,
determine whether the content of the first set of programming instructions is logically valid based on the analysis, wherein if the content of the first set of programming instructions is not logically valid, refusing further receipt of the second set of programming instructions from the computing device until an indication that the computing device has been reset is received, and transmit the first set of programming instructions to the medical device if the content of the first set of programming instructions is logically valid.

12. The system of claim 11, further comprising the medical device, wherein the medical device comprises the mediator module.

13. The system of claim 11, further comprising an intermediate computing device configured to communicate with the computing device and the medical device, wherein the intermediate device comprises the mediator module.

14. The system of claim 13, wherein the intermediate computing device comprises a safe mode interface, wherein the intermediate computing device is configured to transmit alternative instructions to the medical device instead of the first set of programming instructions in response to receiving an input from a user via the safe mode interface.

15. The system of claim 11, wherein the computing device comprises at least one of a patient programming device, a clinician programmer or a personal computer.

16. The system of claim 11, further comprising a watch dog module, wherein the computing device periodically transmits a defined signal to the watch dog module, and wherein the mediator module transmits the first set of programming instructions to the medical device if the defined signal is uninterrupted and transmits alternative instructions to the medical device instead of the first set of programming instructions in response to an interruption in transmission of the defined signal.

17. The system of claim 11, wherein the mediator module is configured to analyze the content of the first set of programming instructions by at least comparing a therapy parameter value set forth by the programming instructions to at least one of a device-specific range of acceptable therapy parameter values, a patient-specific range of acceptable therapy parameter values, or medication dosage instructions.

18. The system of claim 11, further comprising a user interface to interact with the mediator module, wherein the mediator module is configured to prompt a user via the user interface to validate the content of the first set of programming instructions if the content of the first set of programming instructions is not logically valid.

19. A computer-readable medium comprising instructions that cause a processor to:

receive programming instructions for a medical device from a computing device, wherein the programming instructions comprise a first set of programming instructions and a second set of programming instructions;

analyze a content of the first set of programming instructions;

determine whether the content of the first set of programming instructions is logically valid, wherein if the content of the first set of programming instructions is not logically valid, refusing further receipt of the second set of programming instructions from the computing device until an indication that the computing device has been reset is received; and transmit the first set of programming instructions to the medical device if the content of the first set of programming instructions is logically valid.

* * * * *